United States Patent
Kato (10) Patent No.: US 9,165,448 B2
(45) Date of Patent: Oct. 20, 2015

(54) SMOKE DETECTOR

(71) Applicant: NOHMI BOSAI LTD., Tokyo (JP)

(72) Inventor: Kenichi Kato, Tokyo (JP)

(73) Assignee: NOHMI BOSAI LTD., Tokyo (JP)

(*) Notice: Subject to any disclaimer, the term of this patent is extended or adjusted under 35 U.S.C. 154(b) by 104 days.

(21) Appl. No.: 14/016,542

(22) Filed: Sep. 3, 2013

(65) Prior Publication Data

US 2014/0063499 A1    Mar. 6, 2014

(30) Foreign Application Priority Data

Sep. 6, 2012 (JP) ................. 2012-196202

(51) Int. Cl.
  *G01N 21/53* (2006.01)
  *G08B 17/103* (2006.01)
  *G08B 17/107* (2006.01)

(52) U.S. Cl.
  CPC .............. *G08B 17/103* (2013.01); *G01N 21/53* (2013.01); *G08B 17/107* (2013.01)

(58) Field of Classification Search
  CPC ..................................................... G08B 17/103
  See application file for complete search history.

(56) References Cited

U.S. PATENT DOCUMENTS

| | | | | |
|---|---|---|---|---|
| 5,420,440 A * | 5/1995 | Ketler et al. | ................... | 250/573 |
| 7,471,393 B2 * | 12/2008 | Trainer | ................... | 356/336 |
| 8,634,072 B2 * | 1/2014 | Trainer | ................... | 356/335 |
| 8,705,040 B2 * | 4/2014 | Trainer | ................... | 356/450 |
| 2012/0140231 A1 * | 6/2012 | Knox et al. | ................... | 356/442 |

FOREIGN PATENT DOCUMENTS

| | | |
|---|---|---|
| CH | 448 815 | 12/1967 |
| EP | 0 463 795 | 1/1992 |
| WO | 93/08461 | 4/1993 |

OTHER PUBLICATIONS

Extended European Search Report issued Jan. 22, 2014 in corresponding European patent application No. 13 18 3109.

* cited by examiner

*Primary Examiner* — Van Trieu
(74) *Attorney, Agent, or Firm* — Wenderoth, Lind & Ponack, L.L.P.

(57) ABSTRACT

An aperture member (15) is configured to be mounted to a receiving portion (22) provided to a main body (2), and includes a lower surface portion (15a) formed into an arc shape. The receiving portion (22) of the main body (2) includes a bottom surface portion (22a) formed into a shape corresponding to the arc shape of the lower surface portion (15a) of the aperture member (15) so as to be brought into contact with the lower surface portion (15a) of the aperture member (15). The aperture member (15) includes a light passage opening (15e) formed so that a center position (15ea) thereof substantially matches with a position of a center of curvature of the arc shape of the lower surface portion (15a).

16 Claims, 8 Drawing Sheets

SMOKE DETECTOR

BACKGROUND OF THE INVENTION

1. Field of the Invention

The present invention relates to a smoke detector capable of optically detecting smoke, contaminants, and the like floating in the air.

2. Description of the Related Art

Hitherto, there has been used a smoke detector for detecting smoke so as to prevent and extinguish a fire, or for detecting contaminants (dust or the like) so as to preserve an environment in a semiconductor manufacturing plant, a food factory, or the like (so-called clean room or the like).

Among various smoke detectors, there is an optical smoke detector for optically detecting smoke and contaminants contained in the air (hereinafter referred to as "smoke or the like").

The optical smoke detector can detect smoke or the like in such a manner that a light receiving section receives scattered light generated in a smoke detecting section when light emitted from a light emitting section is scattered due to particles of the smoke or the like.

The optical smoke detector is provided with an aperture through which light emitted from the light emitting section passes in order to control the size of the passing region of the light emitted from the light emitting section or prevent generation of stray light (diffracted light). Generally, this aperture is formed integrally with a main body of a case of the smoke detector (for example, see paragraph 0014 and FIGS. 1 to 3, etc. of Japanese Patent Application Laid-open No. Hei 11-248629).

In the smoke detector of this type, it is preferred that a thin aperture that has a small contact area with respect to the passing light be used in terms of preventing generation of diffracted light. Therefore, it is conceivable to reduce the thickness of the aperture.

When the thickness of the aperture is reduced, the strength may become insufficient when the aperture is merely thinned. Therefore, although integral formation of the aperture and the main body becomes impossible, it is conceivable to use another hard material such as an iron plate as an aperture member.

Note that, in the case of the smoke detector of this type, an LED or a laser may be used as a light source of the light emitting section (for example, see paragraph 0012 of Japanese Patent Application Laid-open No. Hei 11-248629). The directionality of light is higher when the laser is used than when the LED is used. In view of preventing generation of diffracted light, it can be said that a greater advantage can be obtained by thinning the aperture.

However, when another material such as an iron plate is used as the aperture member, an operation of mounting the aperture member to the main body is necessary. At this time, an operation of locating the center position of a light passage opening of the aperture member on an optical axis of the light emitting section is necessary.

Further, in order to form the aperture member from the iron plate or the like, piercing is performed to form the light passage opening. Depending on the process method thereof, however, burrs or the like may remain on an opening edge portion of the light passage opening on one surface side in a front-back direction. When the aperture member is mounted to the main body while orienting the surface side on which burrs or the like are liable to remain due to the process toward the light emitting section, if the burrs or the like are left, the burrs or the like may cause generation of diffracted light.

That is, in the case where another material such as an iron plate is used as the aperture member, when the aperture member is assembled to the main body, it is necessary to not only locate the center position of the light passage opening of the aperture member on the optical axis, but also appropriately orient the aperture member in a desired normal direction in the front-back direction (orientation in which, when the surface side in which the burrs or the like are less liable to remain is the front surface side and the surface side in which the burrs or the like are liable to remain is the back surface side, the front surface side is oriented toward the light emitting section, and the back surface side is not directed toward the light emitting section).

SUMMARY OF THE INVENTION

The present invention has been made in view of the above-mentioned circumstances, and has an object to provide a smoke detector in which, when an aperture member is mounted to a main body, a center position of a light passage opening of the aperture member can be easily located on an optical axis of a light emitting section, and in which a front-back direction of the aperture member can be easily oriented to a normal direction.

According to one embodiment of the present invention, there is provided a smoke detector, including: a main body; a light emitting section; a light receiving section; a smoke detecting section, the smoke detector being configured to detect smoke or the like in such a manner that the light receiving section receives scattered light generated when light emitted from the light emitting section is scattered in the smoke detecting section due to particles of the smoke or the like; and an aperture member for narrowing the light emitted from the light emitting section, in which the aperture member is configured to be mounted to a receiving portion provided to the main body, and includes a lower surface portion formed into an arc shape, in which the receiving portion of the main body includes a bottom surface portion formed into a shape corresponding to the arc shape of the lower surface portion of the aperture member so as to be brought into contact with the lower surface portion of the aperture member, and in which the aperture member includes a light passage opening formed so that a center position thereof substantially matches with a position of a center of curvature of the arc shape of the lower surface portion.

Further, according to one embodiment of the present invention, in the smoke detector, the bottom surface portion of the receiving portion of the main body is formed into an arc shape having a radius of curvature substantially equal to a radius of curvature of the arc shape of the lower surface portion of the aperture member.

Further, according to one embodiment of the present invention, in the smoke detector, the aperture member further includes a left outer side surface portion and a right outer side surface portion that are formed into a left-right asymmetric shape, and the receiving portion of the main body further includes a left inner side surface portion and a right inner side surface portion that are formed so that at least one of the left outer side surface portion and the right outer side surface portion of the aperture member is brought into contact thereto.

Further, according to one embodiment of the present invention, in the smoke detector, the left outer side surface portion and the right outer side surface portion of the aperture member are both formed into a linear shape extending along an up-down direction, and formed into a shape having a difference between lengths thereof in the up-down direction.

Further, according to one embodiment of the present invention, in the smoke detector, one of the left outer side surface portion and the right outer side surface portion of the aperture member is formed into a linear shape extending along an up-down direction, and another of the left outer side surface portion and the right outer side surface portion of the aperture member is formed into an arc shape that is continuous with the arc shape of the lower surface portion.

Further, according to one embodiment of the present invention, the smoke detector further includes a lid member to be mounted to the main body. The lid member includes a pressing portion for pressing the aperture member from above, and the pressing portion includes: an abutment portion that abuts against an upper surface portion of the aperture member to press the aperture member from above; and an oblique surface portion that inclines in a front-back direction of the aperture member to be connected to the abutment portion.

Further, according to one embodiment of the present invention, in the smoke detector, the lid member is prevented from being mounted to the main body in a predetermined way when the aperture member is mounted to the receiving portion of the main body while being oriented back to front in a manner opposite to a normal direction.

According to one embodiment of the present invention, the light passage opening of the aperture member is formed so that the center position thereof substantially matches with the position of the center of curvature of the lower surface portion formed into an arc shape. Therefore, when the aperture member is mounted to the receiving portion of the main body, the lower surface portion of the aperture member is brought into contact with the bottom surface portion of the receiving portion of the main body. In this manner, the center position of the light passage opening of the aperture member can be easily located at a predetermined position.

Therefore, according to one embodiment of the present invention, in the smoke detector, when the aperture member is mounted to the main body, the center position of the light passage opening of the aperture member can be easily located on an optical axis of the light emitting section.

Further, according to one embodiment of the present invention, the aperture member further includes the left and right outer side surface portions that are formed into a left-right asymmetric shape, and the receiving portion of the main body further includes the left and right inner side surface portions that are formed so that at least one of the left and right outer side surface portions of the aperture member is brought into contact thereto. In this manner, when the aperture member is mounted to the main body, the desired orientation of the aperture member in the upper, lower, left, and right directions can be easily determined based on the contact relationship between the aperture member and the receiving portion of the main body.

Therefore, according to one embodiment of the present invention, in the smoke detector, when the aperture member is mounted to the main body, the front-back orientation of the aperture member can be easily set to the normal direction.

DETAILED DESCRIPTION OF THE PREFERRED EMBODIMENT

An exemplary embodiment of the present invention is described with reference to FIGS. 1 to 10.

Figure 1:
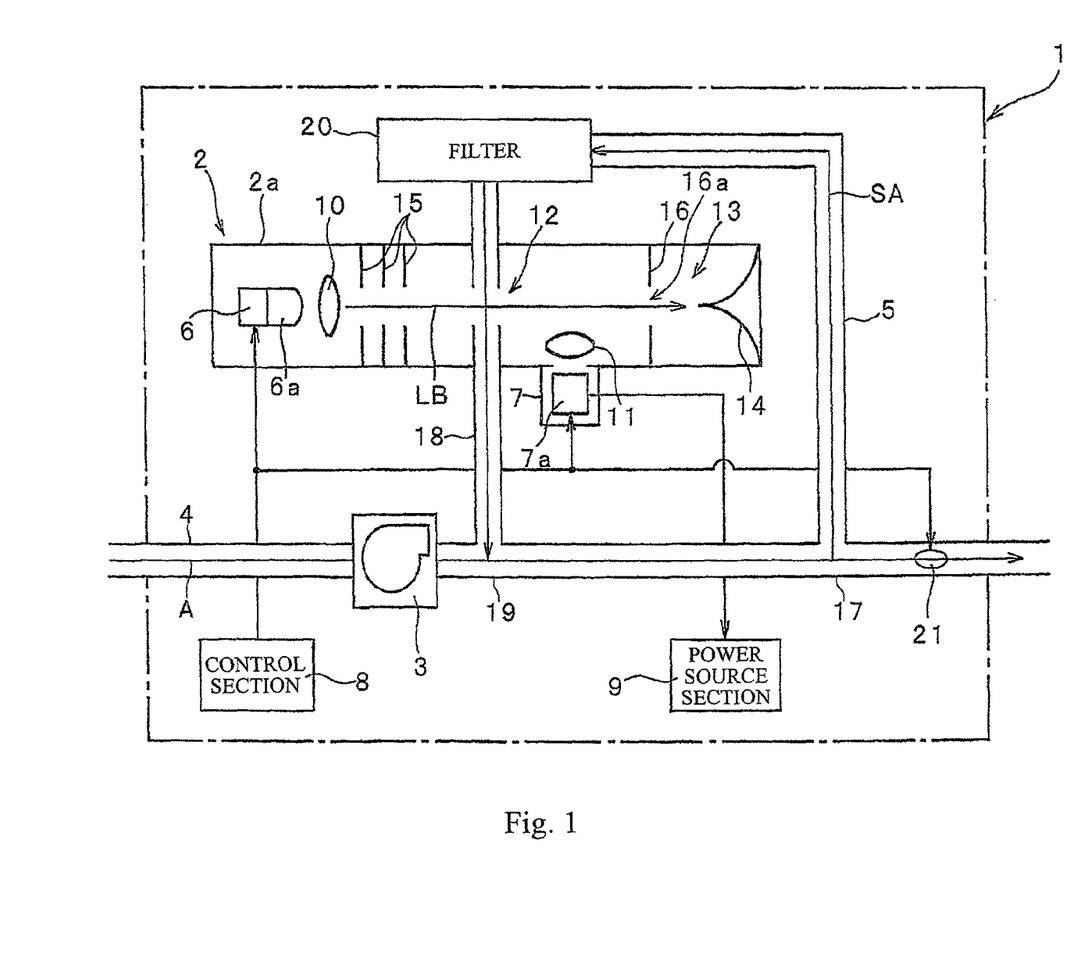
FIG. 1 is a structural view illustrating a schematic structure of an exemplary embodiment of the present invention.
Figure 2:
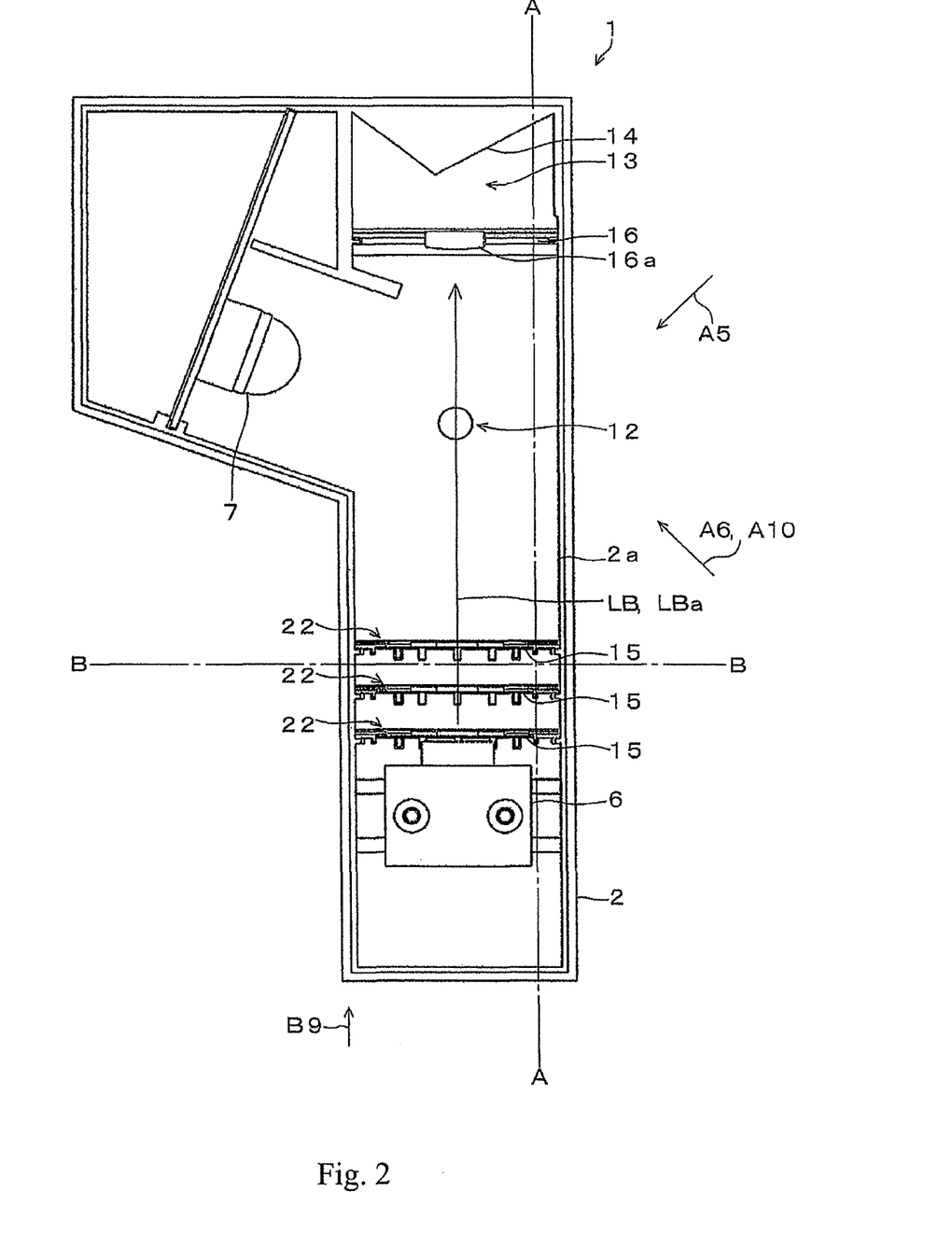
FIG. 2 is a plan view illustrating a main body side of the exemplary embodiment.
Figure 3:
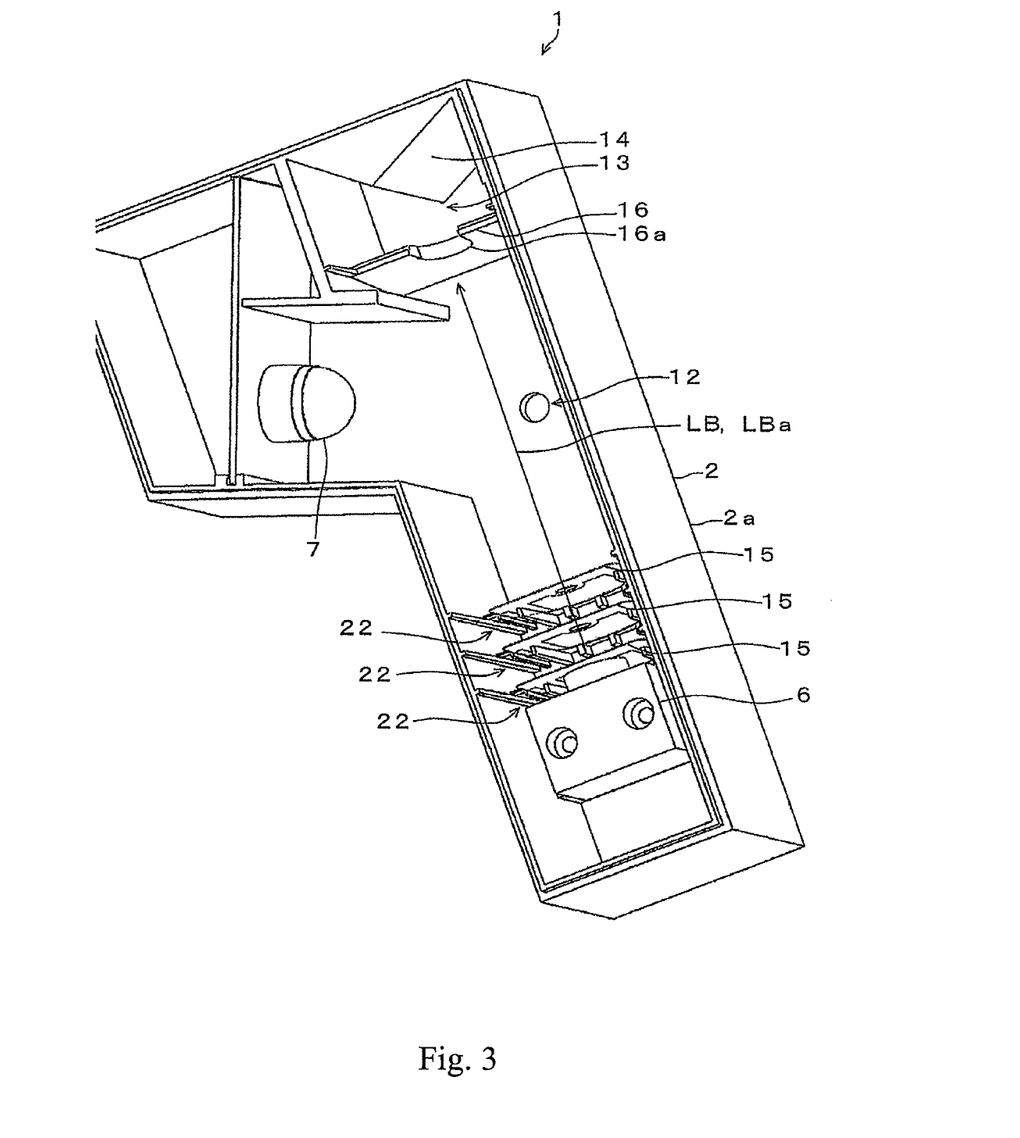
FIG. 3 is a perspective view illustrating the main body side of the exemplary embodiment.
Figure 4:
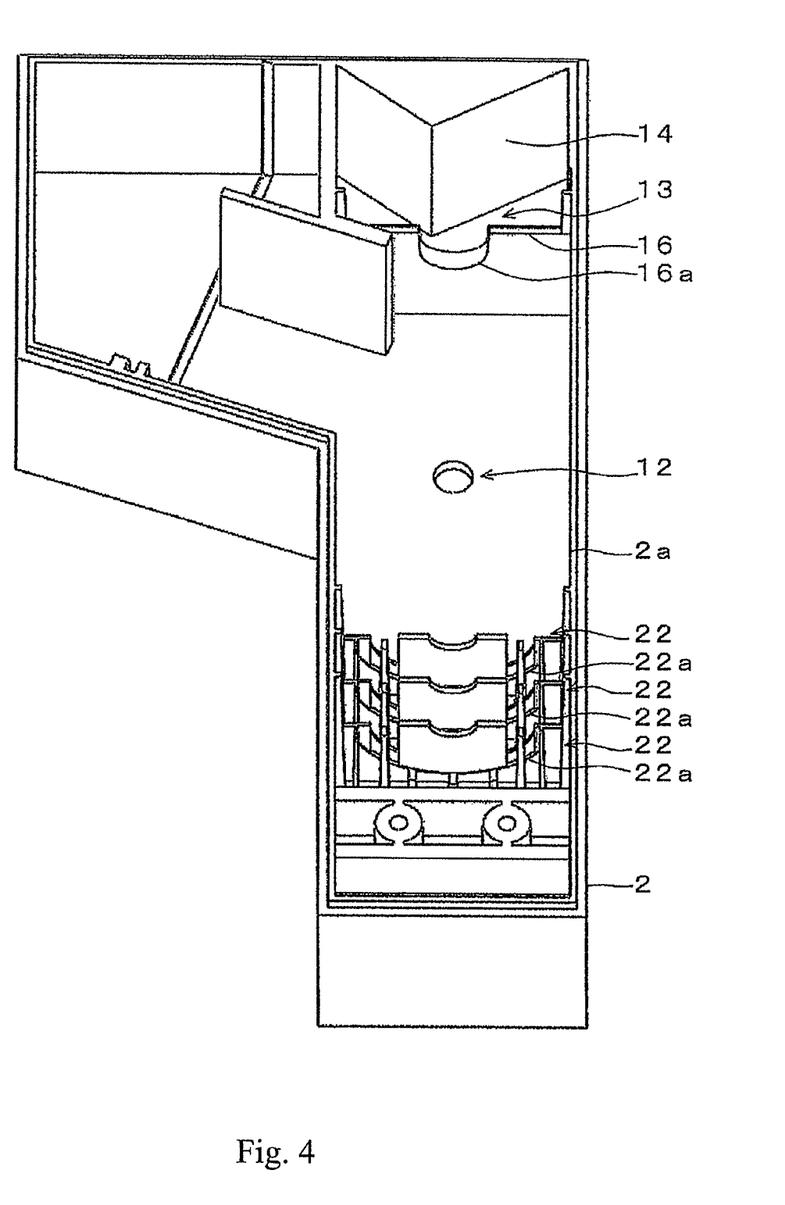
FIG. 4 is a perspective view illustrating the main body side of the exemplary embodiment as viewed from another angle in a state in which an aperture member is not mounted.

First, with reference to FIG. 1, the entire apparatus structure of a smoke detector 1 as the exemplary embodiment of the present invention is schematically described.

As illustrated in FIG. 1, the smoke detector 1 includes, in a smoke detecting unit 2a that becomes a dark box of a main body 2, a light emitting section 6 including a light emitting element 6a such as a laser, a light receiving section 7 including a light receiving element 7a such as a photodiode and arranged so that light LB emitted from the light emitting section 6 does not directly enter the light receiving element 7a, and a smoke detecting section 12 formed in a region including a position at which an optical axis of the light emitting element 6a of the light emitting section 6 and an optical axis of the light receiving element 7a of the light receiving section 7 intersect with each other. When sampling air SA passes through the smoke detecting section 12 inside the smoke detecting unit 2a, smoke or the like is optically detected. That is, if smoke or the like is contained in the sampling air SA, when the sampling air SA passes through the smoke detecting section 12, the light LB emitted from the light emitting element 6a of the light emitting section 6 is scattered in the smoke detecting section 12 due to particles of the smoke or the like so that scattered light is generated. The scattered light thus generated is received by the light receiving element 7a of the light receiving section 7. In this manner, the smoke or the like is detected.

Further, as illustrated in FIG. 1, the smoke detector 1 includes a fan 3 for feeding, as the sampling air SA, air A flowing into the smoke detector 1 via an inlet path 4 through a pipe that is laid in a monitoring zone to the smoke detecting unit 2a via an introduction path 5. Further, the smoke detector 1 includes a power source section 8 connected to components (including an air flow sensor 21) that require a power source, such as the light emitting element 6a of the light emitting section 6 and the light receiving element 7a of the light receiving section 7, and a control section 9 connected to components such as the light emitting element 6a of the light emitting section 6 to perform various control. Still further, the smoke detector 1 includes a light shielding section 13 located on a side opposed to the light emitting section 6 across the smoke detecting section 12, for blocking light so that the light LB emitted from the light emitting element 6a of the light emitting section 6, which has passed through the smoke detecting section 12, does not return to the smoke detecting section 12 side. The light shielding section 13 includes, in a front portion, a light shielding wall 16 having a passage opening 16a formed therein so that the light LB may pass therethrough, and in a back portion, a light trap 14 for attenuating, in the form of stray light, the entering light LB.

Note that, in the smoke detector 1 of this embodiment, the introduction path 5 is branched at a flow path branching section 17 on a secondary side of the fan 3, and a reflux path 18 for causing reflux of the sampling air SA from the smoke detecting unit 2a is joined at a flow path joining section 19 on the secondary side of the fan 3. Due to a pressure difference generated between the flow path joining section 19 and the flow path branching section 17 (the pressure difference may be generated therebetween by setting a flow rate at the flow path joining section 19 higher than a flow rate at the flow path branching section 17; for example, the pressure difference may be generated therebetween by providing the flow path joining section 19 at a position closer to a periphery of rotor blades of the fan 3, and providing the flow path branching section 17 at a position farther from the periphery of the rotor blades of the fan 3), the sampling air SA is caused to pass through the smoke detecting unit 2a from the introduction path 5 while being filtrated with use of a filter 20, and to reflux toward the secondary side of the fan 3 through the reflux path 18.

The smoke detector 1 further includes, in the smoke detecting unit 2a of the main body 2, an aperture member 15 located in front of the light emitting section 6, for narrowing the light LB emitted from the light emitting element 6a of the light emitting section 6 and causing the light LB to pass therethrough toward the smoke detecting section 12. Details of the aperture member 15 are described later with reference to FIGS. 2 to 10.

Note that, the smoke detector 1 illustrated in FIG. 1 includes a condenser lens 10 located immediately in front of the light emitting element 6a of the light emitting section 6, for condensing the light emitted from the light emitting element 6a, and a condenser lens 11 located immediately in front of the light receiving element 7a of the light receiving section 7, for condensing the light entering the light receiving element 7a. Those condenser lenses 10 and 11 are provided inside the light emitting section 6 and the light receiving section 7, respectively, in the smoke detector 1 illustrated in FIGS. 2 to 10.

Next, with reference to FIGS. 2 to 10, details of the apparatus structure of the smoke detector 1 are described.

The smoke detector 1 includes, as described above, the main body 2, the light emitting section 6, the light receiving section 7, and the smoke detecting section 12. The light emitted from the light emitting section 6 (specifically, the light emitting element 6a thereof as illustrated in FIG. 1) is scattered in the smoke detecting section 12 due to particles of the smoke or the like so that scattered light is generated. The scattered light thus generated is received by the light receiving section 7 (specifically, the light receiving element 7a thereof as illustrated in FIG. 1). In this manner, the smoke or the like is detected.

Figure 5:
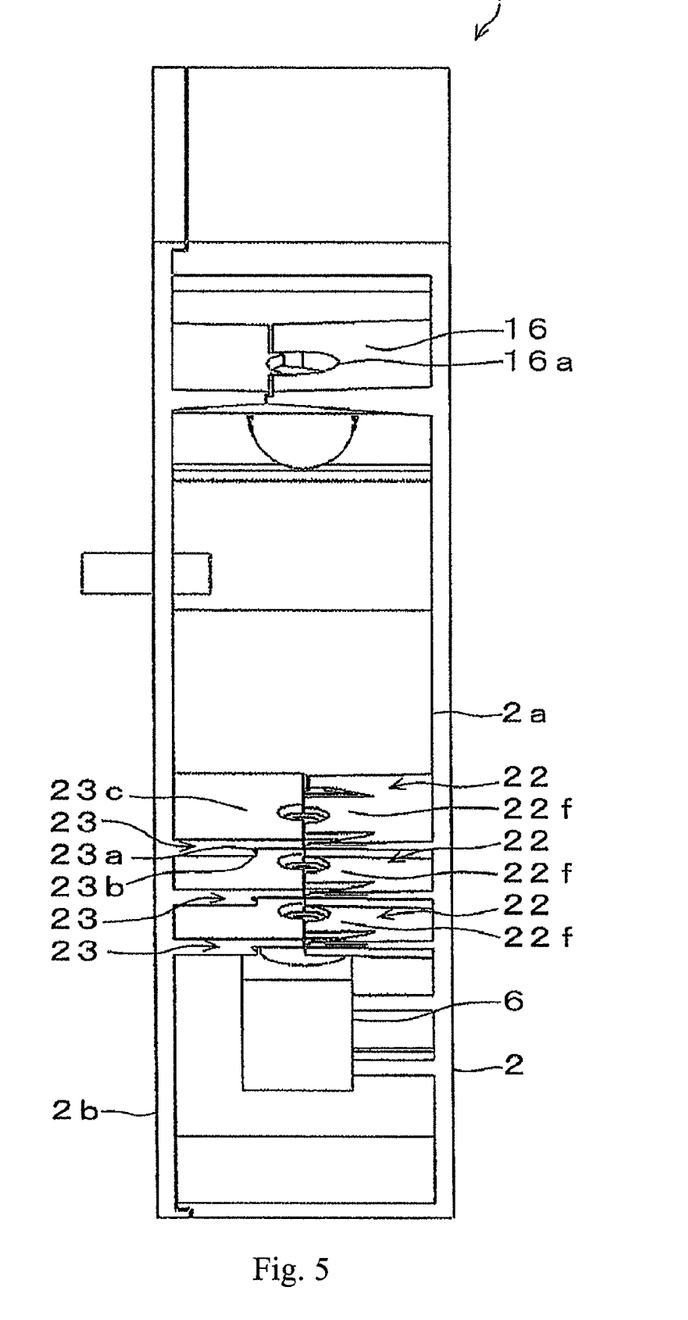
FIG. 5 is a sectional view illustrating the exemplary embodiment, which corresponds to a cross section taken along the line A-A and as viewed from the arrow A5 of FIG. 2, in a state in which a lid member is mounted to the main body.
Figure 6:
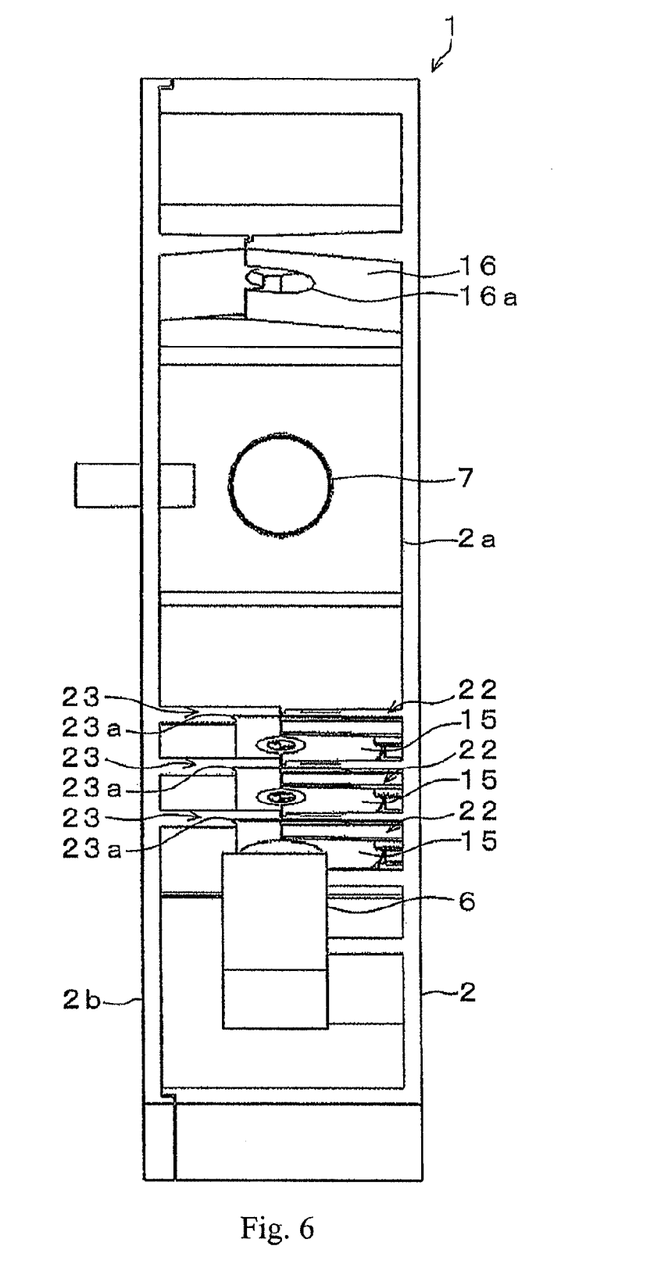
FIG. 6 is a sectional view illustrating the exemplary embodiment, which corresponds to a cross section taken along the line A-A and as viewed from the arrow A6 of FIG. 2, in the state in which the lid member is mounted to the main body.

In this smoke detector 1, as illustrated in FIGS. 2 to 6, the main body 2 has a box shape whose upper portion is opened, and as illustrated in FIGS. 5 and 6, a lid member 2b is mounted to the upper portion to form the dark box. Inside the dark box, the light emitting section 6, the light receiving section 7, the smoke detecting section 12, and the like are provided to form the smoke detecting unit 2a.

Further, the smoke detector 1 further includes, as described above, in the smoke detecting unit 2a of the main body 2, the aperture member 15 located in front of the light emitting section 6, for narrowing the light LB emitted from the light emitting element 6a of the light emitting section 6 and causing the light LB to pass therethrough toward the smoke detecting section 12.

In the smoke detector 1, the aperture member 15 is formed of another hard material such as an iron plate to be thin, and is mounted as another member to a receiving portion 22 provided to the main body 2.

Specifically, the aperture member 15 includes a lower surface portion 15a formed into an arc shape, and left and right outer side surface portions 15b and 15c formed into a left-right asymmetric shape. Further, the receiving portion 22 of the main body 2 includes a bottom surface portion 22a formed into a shape corresponding to the arc shape of the lower surface portion 15a of the aperture member 15 so as to be brought into contact with the lower surface portion 15a, and left and right inner side surface portions 22b and 22c formed into a shape corresponding to the left-right asymmetric shape of the left and right outer side surface portions 15b and 15c of the aperture member 15 so as to be brought into contact with the left and right outer side surface portions 15b and 15c.

In the smoke detector 1, the aperture member 15 and the receiving portion 22 of the main body 2 are formed as described above. Therefore, when the aperture member 15 is mounted to the receiving portion 22 of the main body 2, the lower surface portion 15a of the aperture member 15 is brought into contact with the bottom surface portion 22a of the receiving portion 22 of the main body 2, and the left and right outer side surface portions 15b and 15c of the aperture member 15 are brought into contact with the left and right inner side surface portions 22b and 22c of the receiving portion 22 of the main body 2, respectively. In this manner, the positions of the aperture member 15 in the upper, lower, left, and right directions can be easily located in a predetermined way.

In this case, in the smoke detector 1, as described above, the lower surface portion 15a of the aperture member 15 is formed into an arc shape, and the bottom surface portion 22a of the receiving portion 22 of the main body 2 is formed into a shape corresponding to the arc shape of the lower surface portion 15a of the aperture member 15. Further, the left and right outer side surface portions 15b and 15c of the aperture member 15 are formed into a left-right asymmetric shape, and the left and right inner side surface portions 22b and 22c of the receiving portion 22 of the main body 2 are formed into a shape corresponding to the left-right asymmetric shape of the left and right outer side surface portions 15b and 15c of the aperture member 15. In this manner, when the aperture member 15 is mounted to the receiving portion 22 of the main body 2, based on the correspondence relationship between the shape of the aperture member 15 and the shape of the receiving portion 22 of the main body 2, specifically, based on the correspondence relationship between the shapes of the lower surface portion 15a and the left and right outer side surface portions 15b and 15c of the aperture member 15 and the shapes of the bottom surface portion 22a and the left and right inner side surface portions 22b and 22c of the receiving portion 22 of the main body 2, respectively, the desired orientation of the aperture member 15 in the upper, lower, left, and right directions can be easily determined, that is, the desired orientation of the aperture member 15 in the front-back direction can be easily determined. Therefore, the desired orientation of the aperture member 15 in the front-back direction can be easily obtained.

Note that, in the smoke detector 1, when a light passage opening 15e of the aperture member 15 is processed, depending on the process method thereof, burrs or the like may remain on an opening edge part of the passage opening 15e on one surface side in the front-back direction. To address this problem, as described above, the desired orientation in the front-back direction that is determined based on the correspondence relationship of the shape with respect to the receiving portion 22 is set to the orientation in a normal direction, that is, orientation in which a surface side on which the burrs or the like are less liable to remain, which serves as a front surface 15f, is directed toward the light emitting section 6 and a surface side on which the burrs or the like are liable to remain, which serves as a back surface 15g, is not directed toward the light emitting section 6.

Further, details of the aperture member 15 and the receiving portion 22 of the main body 2 of this embodiment are described.

Figure 7:
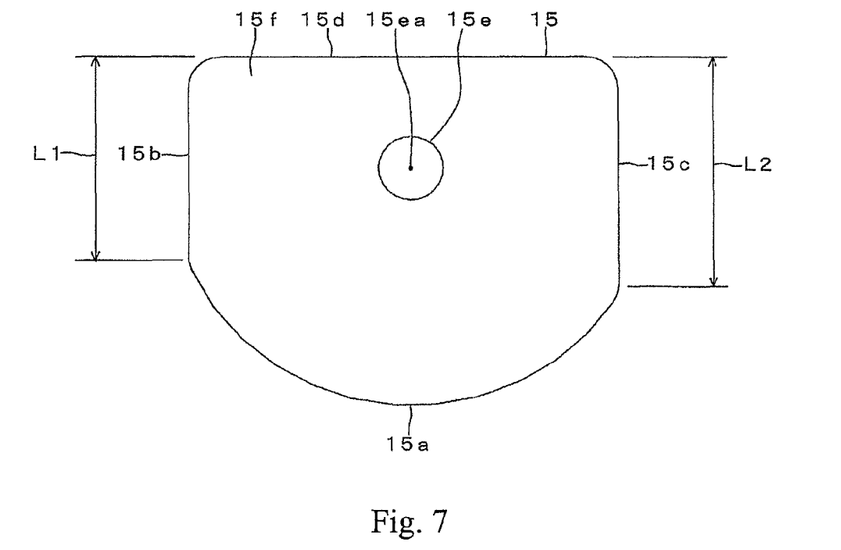
FIG. 7 is an enlarged view illustrating the aperture member of the exemplary embodiment.

In the aperture member 15, the left and right outer side surface portions 15b and 15c formed into a left-right asymmetric shape whose details can be easily understood from the enlarged plan view of FIG. 7 are respectively continuous with left and right upper end portions of the lower surface portion 15a, and both of the left and right outer side surface portions 15b and 15c are formed into a linear shape extending in parallel along an up-down direction. Further, the left and right outer side surface portions 15b and 15c are formed into a shape having a difference between lengths L1 and L2 thereof in the up-down direction (the length L1 of the left outer side surface portion 15b is smaller and the length L2 of the right outer side surface portion 15c is larger). In this manner, the left and right outer side surface portions 15b and 15c are formed into a left-right asymmetric shape. Further, an upper surface portion 15d is formed into a linear shape extending in parallel along a width direction and provided continuously with the respective upper end portions of the left and right outer side surface portions 15b and 15c via rounded corner portions.

In the aperture member 15, a center position 15ea of the light passage opening 15e is decentered from a center position in the upper, lower, left, and right directions of the aperture member 15, but is formed to match with the position of a center of curvature of the lower surface portion 15a.

In this case, in the smoke detector 1, as described above, the center position 15ea of the light passage opening 15e of the aperture member 15 is formed to substantially match with the position of the center of curvature of the lower surface portion 15a formed into an arc shape. As a result, combined with the fact that the bottom surface portion 22a of the receiving portion 22 of the main body 2 is formed into a shape corresponding to the arc shape of the lower surface portion 15a, when the aperture member 15 is mounted to the receiving portion 22 of the main body 2, the lower surface portion 15a of the aperture member 15 is brought into contact with the bottom surface portion 22a of the receiving portion 22 of the main body 2. In this manner, the center position 15ea of the light passage opening 15e of the aperture member 15 can be easily located at a predetermined position, and can be easily located on an optical axis LBa of the light emitting section 6.

Figure 8:
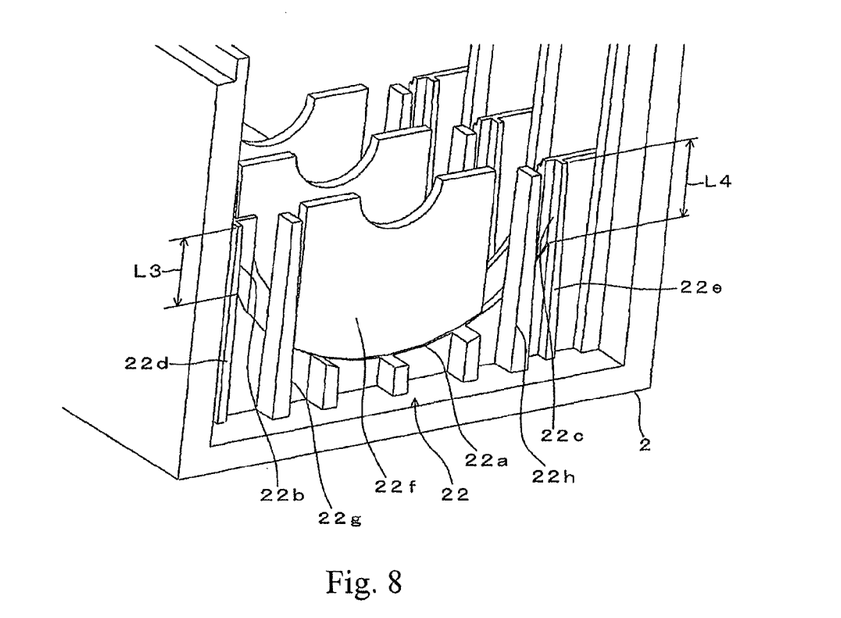
FIG. 8 is an enlarged perspective view illustrating an aperture member mounting part of the main body of the exemplary embodiment.

The receiving portion 22 whose details can be most easily understood from the enlarged perspective view of FIG. 8 is formed as a part forming a wall as a whole, which is provided upright on a bottom wall of the main body 2. On left and right outer sides of the bottom surface portion 22a, left and right side wall portions 22d and 22e are provided, and on inner side surfaces thereof, the left and right inner side surface portions 22b and 22c are provided so as to be continuous with the upper portion of the bottom surface portion 22a. Further, a back wall portion 22f for supporting the back surface 15g side (side not directed toward the light emitting section 6) of the aperture member 15 is provided at a center position in the width direction (a semicircular cutout portion is provided at the center of the upper portion so as not to block the passage opening 15e of the aperture member 15). Still further, left and right support columns 22g and 22h for supporting the front surface 15f side (side directed toward the light emitting section 6) of the aperture member 15 are respectively provided slightly closer to the center with respect to the left and right side wall portions 22d and 22e.

The receiving portion 22 is formed as follows. As described above, the bottom surface portion 22a is formed into a shape corresponding to the arc shape of the lower surface portion 15a of the aperture member 15, and in this embodiment, the bottom surface portion 22a is formed into an arc shape having a radius of curvature substantially equal to the radius of curvature of the arc shape of the lower surface portion 15a of the aperture member 15. In addition, the arc length of the bottom surface portion 22a is formed to be substantially equal to the arc length of the lower surface portion 15a of the aperture member 15. Therefore, when the aperture member 15 is mounted to the receiving portion 22 while being oriented in the normal direction, the bottom surface portion 22a is brought into close contact with the lower surface portion 15a of the aperture member 15 over the entire length in the circumferential direction without a gap. Further, the position of the center of curvature of the bottom surface portion 22a is located on the optical axis LBa of the light emitting section 6, and hence when the aperture member 15 is mounted to the receiving portion 22 while being oriented in the normal direction, the position of the center of curvature thereof substantially matches with the position of the center of curvature of the lower surface portion 15a of the aperture member 15, and the center position 15ea of the light passage opening 15e of the aperture member 15 is automatically located on the optical axis LBa of the light emitting section 6.

Further, in the receiving portion 22, as described above, the left and right inner side surface portions 22b and 22c are formed into a shape corresponding to the left-right asymmetric shape of the left and right outer side surface portions 15b and 15c of the aperture member. Further, in this embodiment, the left and right inner side surface portions 22b and 22c are separated from each other at an interval having a length substantially equal to the length of the aperture member 15 in the width direction. Further, similarly to the left and right outer side surface portions 15b and 15c of the aperture member 15, both of the left and right inner side surface portions 22b and 22c are formed into a linear shape extending in parallel along the up-down direction, and are formed into a shape having a difference between lengths L3 and L4 thereof in the up-down direction (see FIG. 8). The left inner side surface portion 22b having the smaller length L3 corresponds to the left outer side surface portion 15b having the smaller length L1 of the aperture member 15, and the right inner side surface portion 22c having the larger length L4 corresponds to the right outer side surface portion 15c having the larger length L2 of the aperture member 15.

Note that, in this embodiment, in the left and right inner side surface portions 22b and 22c of the receiving portion 22 described above, the length L3 of the smaller left inner side surface portion 22b is about half the length L1 of the corresponding smaller left outer side surface portion 15b of the aperture member 15, and the length L4 of the larger right inner side surface portion 22c is about half the length L2 of the corresponding larger right outer side surface portion 15c of the aperture member 15. Therefore, when the aperture member 15 is mounted to the receiving portion 22 while being oriented in the normal direction, the left and right outer side surface portions 15b and 15c of the aperture member 15 are brought into close contact with the respective left and right inner side surface portions 22b and 22c without a gap up to the lower half thereof in the length direction.

Figure 9:
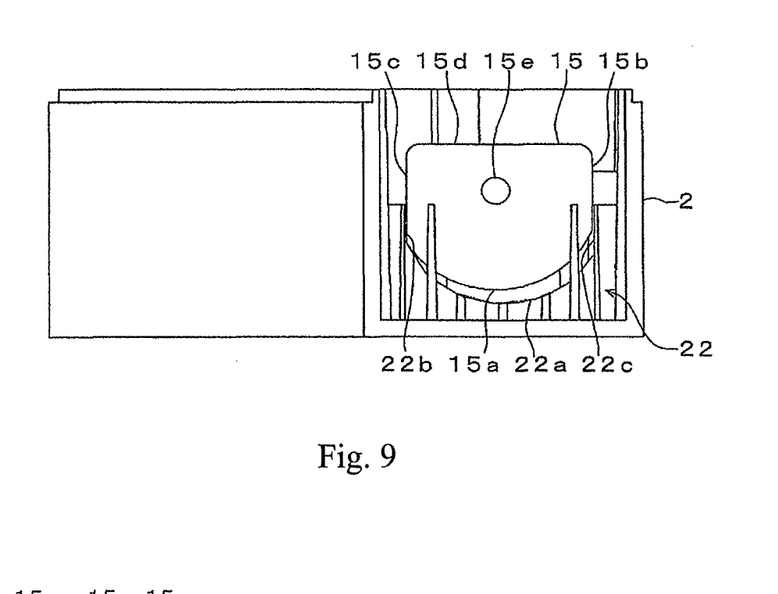
FIG. 9 is a sectional view illustrating the exemplary embodiment, which is taken along the line B-B and as viewed from the arrow B9 of FIG. 2, in a state in which the aperture member is mounted back to front (in reverse orientation)
Figure 10:
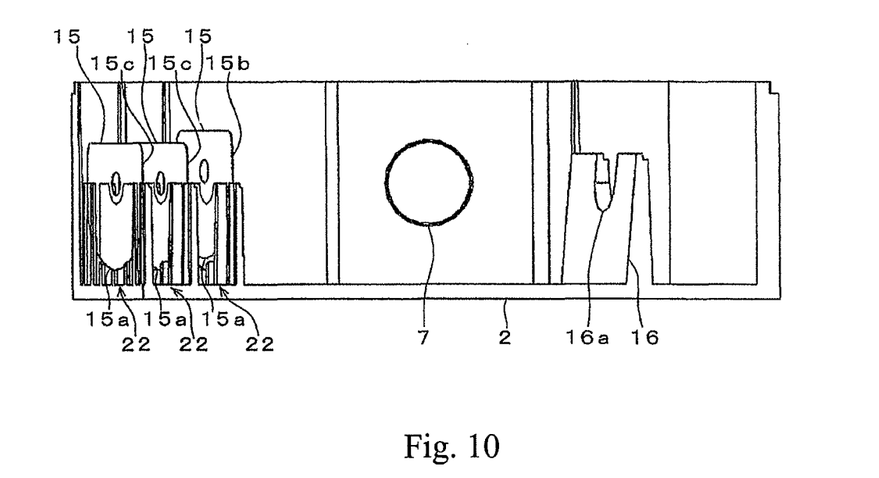
FIG. 10 is a sectional view illustrating the exemplary embodiment, which is taken along the line A-A and as viewed from the arrow A10 of FIG. 2, in the state in which the aperture member is mounted back to front (in reverse orientation).

The aperture member 15 and the receiving portion 22 of the main body 2 are formed so that, as described above, when the aperture member 15 is mounted to the receiving portion 22 while being oriented in the normal direction, the lower surface portion 15a and the left and right outer side surface portions 15b and 15c of the aperture member 15 are brought into close contact with the bottom surface portion 22a and the left and right inner side surface portions 22b and 22c of the receiving portion 22, respectively, without a gap. However, when the aperture member 15 is mounted to the receiving portion 22 while being oriented back to front in a manner opposite to the normal direction, the position of the center of curvature of the lower surface portion 15a of the aperture member 15 and the position of the center of curvature of the bottom surface portion 22a of the receiving portion 22 do not match with each other. As a result, a gap is generated therebetween as illustrated in FIGS. 9 and 10, and the aperture member 15 is upwardly lifted to protrude upwardly from a predetermined position. With this, it can be easily determined that the aperture member 15 is oriented back to front in a manner opposite to the normal direction.

Note that, in this embodiment, when the aperture member 15 is mounted to the receiving portion 22 of the main body 2, the left and right outer side surface portions 15b and 15c of the aperture member 15 and the left and right inner side surface portions 22b and 22c of the receiving portion 22 of the main body 2 can be respectively brought into contact with each other both on left and right sides whether the front and back sides are in the normal direction or in the opposite direction, but may be formed so that only one of the left and right sides can establish the contact. When the aperture member 15 is mounted to the receiving portion 22 of the main body 2 while being oriented back to front, only one of the left and right sides may establish the contact, to thereby, similarly to the above, generate a gap between the lower surface portion 15a of the aperture member 15 and the bottom surface portion 22a of the receiving portion 22 so that the aperture member 15 is upwardly lifted to protrude upwardly from a predetermined position (even when the aperture member 15 is mounted to the receiving portion 22 of the main body 2 while being oriented in the front-back normal direction, in a case where only one of the left and right sides establishes the contact, the aperture member 15 may be rotated, but when there is provided a pressing member from above, such as a pressing portion 23 of the lid member 2b to be described later, the aperture member 15 may be corrected to a predetermined angle position).

On the upper portion of the main body 2, as illustrated in FIGS. 5 and 6, the lid member 2b is mounted. On the lid member 2b, the pressing portion 23 for pressing the aperture member 15 from above is provided so as to, by pressing from above, reliably fix the aperture member 15 mounted to the receiving portion 22 of the main body 2.

Specifically, the pressing portion 23 is provided so as to hang down from an inner surface of the lid member 2b, and is formed as a part having a wall shape. The pressing portion 23 includes an abutment portion 23a that is opposed to and abuts against the upper surface portion 15d of the aperture member 15 from above to press the aperture member 15 from above, and an oblique surface portion 23b that inclines backward and upward in the front-back direction of the aperture member 15 to be connected to the abutment portion 23a located at the top portion thereof. By mounting the lid member 2b to the main body 2, the pressing portion 23 can press the aperture member 15 from above. Further, when the lid member 2b is mounted to the main body 2, the upper surface portion 15d of the aperture member 15 can be slid on the oblique surface portion 23b toward the abutment portion 23a so that the upper surface portion 15d can be guided to reach the abutment portion 23a.

Note that, the pressing portion 23 includes a back wall portion 23c for supporting the aperture member 15 from the back surface 15g side (a semicircular cutout portion is provided at the center position of the lower end so as not to block the passage opening 15e of the aperture member 15 similarly to the back wall portion 22f of the receiving portion 22). Further, the abutment portion 23a and the oblique surface portion 23b are integrally provided on the upper portion of the back wall portion 23c on the front surface side.

As described above, the lid member 2b includes the pressing portion 23 for the aperture member 15, and by mounting the lid member 2b, the abutment portion 23a of the pressing portion 23 abuts against the upper surface portion 15d of the aperture member 15 so as to press the aperture member 15 from above. When the aperture member 15 is mounted to the receiving portion 22 while being oriented in the front-back normal direction, the lid member 2b can be completely mounted to the main body 2 while pressing the aperture member 15 from above by the abutment portion 23a of the pressing portion 23 (state illustrated in FIGS. 5 and 6). However, when the aperture member 15 is mounted to the receiving portion 22 while being oriented back to front in a manner opposite to the normal direction, the aperture member 15 is in an upwardly lifted state, and hence the position of the upper surface portion 15d is raised (state illustrated in FIGS. 9 and 10). In this state, the lid member 2b cannot be completely mounted to the main body 2. In this manner, it can be easily determined that the aperture member 15 is oriented back to front in a manner opposite to the normal direction. Thus, it is possible to prevent the product to be shipped in this state.

Finally, in this embodiment, a plurality of, specifically, three receiving portions 22 are provided in the main body 2 so as to be arrayed at predetermined intervals in the front-back direction at positions in front of the light emitting section 6. Further, a plurality of, specifically, three aperture members 15 are mounted.

Note that, only a single aperture member 15 may be mounted, but by mounting a plurality of aperture members, diffracted light, which may be generated at the opening edge of the passage opening 15e on the back surface side that is not directed toward the light emitting section 6, can be attenuated every time the diffracted light passes through the aperture member 15 (when three aperture members are mounted as in this embodiment, the diffracted light can be sufficiently attenuated).

In the above, the embodiment of the present invention has been described in detail, but the present invention is not limited to the above-mentioned embodiment, and various changes are possible within the range not departing from the spirit of the present invention.

For example, the left-right asymmetric shape of the left and right outer side surface portions 15b and 15c of the aperture member 15 may be formed into a shape in which one of the left and right circular sides is cut off. Specifically, one of the left and right outer side surface portions 15b and 15c may be formed into a linear shape extending along the up-down direction, and the other thereof may be formed into an arc shape that is continuous with the arc shape of the lower surface portion 15a and has the same radius of curvature as that of the lower surface portion 15a.

What is claimed is:

1. A smoke detector, comprising:
    a main body;
    a light emitting section;
    a light receiving section;
    a smoke detecting section,
        the smoke detector being configured to detect smoke or contaminants in such a manner that the light receiving section receives scattered light generated when light emitted from the light emitting section is scattered in the smoke detecting section due to particles of the smoke or the contaminants; and
    an aperture member for narrowing the light emitted from the light emitting section,
    wherein the aperture member is configured to be mounted to a receiving portion provided to the main body, and comprises a lower surface portion formed into an arc shape,
    wherein the receiving portion of the main body comprises a bottom surface portion formed into a shape corresponding to the arc shape of the lower surface portion of the aperture member so as to be brought into contact with the lower surface portion of the aperture member, and
    wherein the aperture member comprises a light passage opening formed so that the light passage opening is decentered from a center position in the upper, lower, left, and right directions of the aperture member, but a center position thereof substantially matches with a position of a center of curvature of the arc shape of the lower surface portion.

2. A smoke detector according to claim 1, wherein the bottom surface portion of the receiving portion of the main body is formed into an arc shape having a radius of curvature substantially equal to a radius of curvature of the arc shape of the lower surface portion of the aperture member.

3. A smoke detector according to claim 2,
    wherein the aperture member further comprises a left outer side surface portion and a right outer side surface portion that are formed into a left-right asymmetric shape, and
    wherein the receiving portion of the main body further comprises a left inner side surface portion and a right inner side surface portion that are formed so that at least one of the left outer side surface portion and the right outer side surface portion of the aperture member is brought into contact thereto.

4. A smoke detector according to claim 3, wherein the left outer side surface portion and the right outer side surface portion of the aperture member are both formed into a linear shape extending along an up-down direction, and formed into a shape having a difference between lengths thereof in the up-down direction.

5. A smoke detector according to claim 3, wherein one of the left outer side surface portion and the right outer side surface portion of the aperture member is formed into a linear shape extending along an up-down direction, and another of the left outer side surface portion and the right outer side surface portion of the aperture member is formed into an arc shape that is continuous with the arc shape of the lower surface portion.

6. A smoke detector according to claim 1,
    wherein the aperture member further comprises a left outer side surface portion and a right outer side surface portion that are formed into a left-right asymmetric shape, and
    wherein the receiving portion of the main body further comprises a left inner side surface portion and a right inner side surface portion that are formed so that at least one of the left outer side surface portion and the right outer side surface portion of the aperture member is brought into contact thereto.

7. A smoke detector according to claim 6, wherein the left outer side surface portion and the right outer side surface portion of the aperture member are both formed into a linear shape extending along an up-down direction, and formed into a shape having a difference between lengths thereof in the up-down direction.

8. A smoke detector according to claim 6, wherein one of the left outer side surface portion and the right outer side surface portion of the aperture member is formed into a linear shape extending along an up-down direction, and another of the left outer side surface portion and the right outer side surface portion of the aperture member is formed into an arc shape that is continuous with the arc shape of the lower surface portion.

9. A smoke detector, comprising:
    a main body;
    a light emitting section;
    a light receiving section;
    a smoke detecting section,
        the smoke detector being configured to detect smoke or contaminants in such a manner that the light receiving section receives scattered light generated when light emitted from the light emitting section is scattered in the smoke detecting section due to particles of the smoke or the contaminants; and
    an aperture member for narrowing the light emitted from the light emitting section,
    wherein the aperture member is configured to be mounted to a receiving portion provided to the main body, and comprises a lower surface portion formed into an arc shape,
    wherein the receiving portion of the main body comprises a bottom surface portion formed into a shape corresponding to the arc shape of the lower surface portion of the aperture member so as to be brought into contact with the lower surface portion of the aperture member, and
    wherein the aperture member comprises a light passage opening formed so that the light passage opening is decentered from a center position in the upper, lower, left, and right directions of the aperture member, but a center position thereof substantially matches with a position of a center of curvature of the arc shape of the lower surface portion,
    further comprising a lid member to be mounted to the main body,
    wherein the lid member comprises a pressing portion for pressing the aperture member from above, and
    wherein the pressing portion comprises:

an abutment portion that abuts against an upper surface portion of the aperture member to press the aperture member from above; and an oblique surface portion that inclines in a front-back direction of the aperture member to be connected to the abutment portion.

10. A smoke detector according to claim 9, wherein the lid member is prevented from being mounted to the main body in a predetermined way when the aperture member is mounted to the receiving portion of the main body while being oriented back to front in a manner opposite to a normal direction.

11. A smoke detector according to claim 9, wherein the bottom surface portion of the receiving portion of the main body is formed into an arc shape having a radius of curvature substantially equal to a radius of curvature of the arc shape of the lower surface portion of the aperture member.

12. A smoke detector according to claim 11, wherein the lid member is prevented from being mounted to the main body in a predetermined way when the aperture member is mounted to the receiving portion of the main body while being oriented back to front in a manner opposite to a normal direction.

13. A smoke detector according to claim 11,
wherein the aperture member further comprises a left outer side surface portion and a right outer side surface portion that are formed into a left-right asymmetric shape, and
wherein the receiving portion of the main body further comprises a left inner side surface portion and a right inner side surface portion that are formed so that at least one of the left outer side surface portion and the right outer side surface portion of the aperture member is brought into contact thereto.

14. A smoke detector according to claim 13, wherein the lid member is prevented from being mounted to the main body in a predetermined way when the aperture member is mounted to the receiving portion of the main body while being oriented back to front in a manner opposite to a normal direction.

15. A smoke detector according to claim 9,
wherein the aperture member further comprises a left outer side surface portion and a right outer side surface portion that are formed into a left-right asymmetric shape, and
wherein the receiving portion of the main body further comprises a left inner side surface portion and a right inner side surface portion that are formed so that at least one of the left outer side surface portion and the right outer side surface portion of the aperture member is brought into contact thereto.

16. A smoke detector according to claim 15, wherein the lid member is prevented from being mounted to the main body in a predetermined way when the aperture member is mounted to the receiving portion of the main body while being oriented back to front in a manner opposite to a normal direction.

* * * * *